United States Patent [19]
McKinnie et al.

[11] Patent Number: 5,347,053
[45] Date of Patent: Sep. 13, 1994

[54] PROCESS FOR PREPARING ALKYLAMINES

[75] Inventors: Bonnie G. McKinnie, Magnolia, Ark.; W. Brian Harrod, Minden, La.

[73] Assignee: Albemarle Corporation, Richmond, Va.

[21] Appl. No.: 971,085

[22] Filed: Nov. 4, 1992

[51] Int. Cl.$^5$ .................................... C07C 209/08
[52] U.S. Cl. ................................ 564/481; 564/445
[58] Field of Search ................... 564/481, 445

[56] References Cited

U.S. PATENT DOCUMENTS

| | | | |
|---|---|---|---|
| 3,294,851 | 12/1966 | Roobol et al. | 260/652 |
| 3,385,893 | 5/1968 | Wakeman | 564/481 |
| 3,471,561 | 10/1969 | Dadekian et al. | 260/583 |
| 3,471,562 | 10/1969 | Wakeman et al. | 260/583 |
| 3,476,807 | 11/1969 | Johnston et al. | 260/583 |
| 3,497,555 | 2/1970 | Dudzinski | 260/583 |
| 3,542,876 | 11/1970 | Blaney | 260/583 |
| 3,728,393 | 4/1973 | Gaige et al. | 260/585 A |
| 3,764,626 | 10/1973 | Pivette | 260/583 R |
| 3,852,258 | 12/1974 | Flay | 260/585 A |
| 4,024,189 | 5/1977 | Davis | 260/585 A |
| 4,982,024 | 1/1991 | Lin et al. | 570/262 |

*Primary Examiner*—Richard L. Raymond
*Assistant Examiner*—Scott C. Rand
*Attorney, Agent, or Firm*—Richard J. Hammond

[57] ABSTRACT

This invention relates to an improvement in a process for producing an alkylamine from olefin and amine by hydrohalogenating the olefin to form haloalkane then reacting the haloalkane with amine to form an alkylamine. The improvement comprises heat-treating the alkylamine thus formed with an aqueous alkaline or alkaline earth metal hydroxide at a temperature and for a period of time sufficient to minimize the formation of flocculent precipitate during the formation and/or storage of the alkylamine.

18 Claims, No Drawings

PROCESS FOR PREPARING ALKYLAMINES

BACKGROUND

This invention relates to an improved process for the preparation of alkylamine from olefin by first hydrohalogenating the olefin to form haloalkane then reacting the haloalkane with amine to form alkylamine. The alkylamine, thus formed, is then heat-treated with an aqueous alkaline or alkaline earth metal hydroxide at a temperature and for a period of time sufficient to minimize the formation of flocculent precipitate during product storage.

As a class, many alkylamines and products derived therefrom, especially linear tertiary amines, are useful as surface active agents, e.g., surfactants, soaps, cleansing agents, and other personal care products. Processes for the formation of alkylamines are known. U.S. Pat. No. 4,024,189 discloses one such process and is incorporated herein by reference as if fully set forth, wherein alkylamines, most notably alkyldimethylamines, are produced starting with a mixed olefin feed, which may contain vinyl olefins and internal olefins, or vinyl olefins and vinylidene olefins, or a mixture of vinyl olefins, internal olefins and vinylidene olefins.

Initially, where vinylidene olefins are present in appreciable amounts, the olefin feed can be selectively isomerized to convert the vinylidene olefins to branched chain internal olefins. The mixture of vinyl olefins and internal olefins is then hydrohalogenated in the presence of a free radical catalyst to produce haloalkanes. The haloalkanes are then selectively dehydrohalogenated whereby 1-haloalkanes are substantially unaffected while secondary haloalkanes are converted to olefins and separated from the 1-haloalkanes. Amination of the 1-haloalkanes is conducted with an amine having at least one replaceable hydrogen atom, thus converting the 1-haloalkanes to amine hydrohalides. Following this operation, the amine hydrohalides in the intermediate product are converted into amines, preferably by a neutralization reaction with a suitable base thus forming a halide salt of the base used in neutralization. The amines thus produced are recovered from the halide salt.

U.S. Pat. No. 4,982,024 discloses a process for the selective dehydrohalogenation of a feed comprised of a mixture of primary, secondary and tertiary alkylbromides; conversion of the secondary and tertiary alkylbromides to olefins, with minimal conversion, if any, of the primary alkylbromides; and simultaneous separation of primary alkylbromides from the reaction mixture. This process allows for the use of more mixed olefin feeds rather than the high purity alpha olefin feeds required for use in the process disclosed in U.S. Pat. No. 4,024,189.

In both of the aforementioned processes, a considerable amount of flocculent precipitate (hereinafter referred to as "floc") tends to form during long term storage of the alkylamine (ADMA) product. Floc occurs in ADMA samples in either of two main descriptive forms. The first form is a "blue haze" which appears in product column feed and or distillate samples. The second form of floc appears as a solid precipitate in the bottom of samples bottles, which may occur in the samples after a few days of storage. The floc has been identified as a quaternary ammonium salt, which is believed to be n-alkyltrimethylammonium halide and/or dialkyldimethylammonium halide or mixtures thereof which is relatively insoluble in the alkylamine products. It is theorized, although the process of this invention is not bound by such theory, that much of the floc is formed by the reaction of the alkylamine product with an alkyl bromide that inadvertently co-distills with the alkylamine product. The formation of quaternary ammonium salts, commonly proceeds by the Menschutkin reaction, as exemplified in Equation I for quaternary ammonium bromides.

$$R_3N + RBr \iff R_4N^+ + Br^-  \quad (I)$$

During long term storage and/or overseas transportation of the alkylamine product, the product may react with the alkyl bromide to form the insoluble quaternary ammonium salts. Precipitation of the salts thus formed tends to give the product a cloudy appearance. Therefore, there exists a clear and present need for processes which reduce the amount of floc which forms during the storage of alkylamines.

It is, accordingly, a primary objective of this invention to fulfill this need, and others. In particular, it is an objective to provide for an improvement to well known prior art methods for producing alkylamines so as to substantially reduce the tendency to form floc when the product is transported or stored.

THE INVENTION

This invention provides, for the first time, an improvement in a process for producing alkylamine from olefin by hydrohalogenating olefin to form haloalkane then reacting the haloalkane thus formed with amine to form alkylamine. The improvement comprises post-treating the alkylamine thus formed with an aqueous alkaline or alkaline earth metal hydroxide at a temperature and for a period of time sufficient to minimize the formation of flocculent precipitate during storage of the alkylamine.

The invention also relates to a method for reducing the potential for forming flocculent precipitate during the manufacture and/or storage of alkylamines. This method entails heat-treating an alkylamine in the presence of an alkaline or alkaline earth metal hydroxide at a temperature and for a period of time sufficient to minimize the formation of flocculent precipitate during manufacture and/or storage of the alkylamine.

Additionally, this invention relates to an alkylamine product having reduced flocculent precipitate-forming characteristics produced by the aforementioned process.

Accordingly, it has been discovered, quite surprisingly, that the contact of alkylamines with aqueous alkali or alkaline earth metal hydroxides at elevated temperatures for a sufficient period of time is particularly effective in reducing the amount of floc formation in the alkylamine product during manufacture and/or storage of the alkylamine.

A particular advantage of this invention is that the process allows for the recovery of an improved alkylamine product which has less tendency to form floc during storage without the need for expensive and time-consuming floc separation techniques. Other advantages include an increase in the product filtration rates and a decrease in the turbidity of the stored product.

For the purposes of this invention, the alkylamine products disclosed herein are represented by the formula,

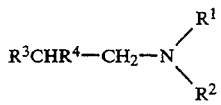

wherein each of $R^1$, $R^2$, $R^3$, and $R^4$ is hydrogen or alkyl having from 1 to about 24 carbon atoms. Examples of preferred alkylamines include lauryl dimethylamine, didecyl methylamine, tetradecyl dimethylamine, hexadecyl dimethylamine, lauryl diisopropylamine, tetradecyl diisopropyl-amine, hexadecyl diisopropylamine, dilauryl methylamine, ditetra-decyl methylamine, dihexadecyl methylamine, dilauryl isopropyl-amine, ditetradecyl isopropylamine, dihexadecyl isopropylamine, and the like.

The alkylamine products of this invention may be prepared by reaction of alkylhalides with $C_8$ to $C_{18}$ alcohols or by hydrohalogenating olefins with HBr. Preferably, the alkylamines are prepared from olefins of the formula $$R^3CR^4=CH_2 \qquad (III)$$

in admixture with internal olefins of the formula $$R^5CR^6=CHR^7 \qquad (IV)$$

wherein each of $R^3$, $R^4$, and $R^6$ is hydrogen or alkyl having from 1 to about 24 carbon atoms, and each of $R^5$ and $R^7$ is an alkyl group having from 1 to about 24 carbon atoms.

Typical olefinic reactants useful in this invention 2O include vinyl olefins such as propylene, butene-1, pentene-1, hexene-1, octene-1, nonene-1, decene-1, undecene-1, dodecene-1, tridecene-1, tetradecene-1, pentadecene-1, hexadecene-1, heptadecene-1, octadecene-1, nonadecene-1, eicosene-1, and corresponding isomeric vinylidene and internal olefins, individually as well as in various combinations of two or more different molecular weights. Usual olefin mixtures are isomers having the same molecular weight since the separation of isomeric olefins of the same molecular weight by simple processes such as distillation is difficult. Where the feed olefins contain remote branching, i.e., at carbon atoms which are not linked to the olefinic double bonds, they react in the present process and produce products analogous to the vinyl olefins. A typical branched, vinylidene, terminal olefin which can be used containing an alkyl group is 2-ethyldodecene. Preferred olefins are unsubstituted or contain only compatible substitution such as alkyl groups and the like which do not undergo adverse or undesirable side reactions in the process. Preferably, the olefin reactant is a lower olefin. By lower olefin is meant an olefin having 3 to 24 carbon atoms; more preferably, an olefin having 4 to 20 carbon atoms; and most preferably, a $C_8$ to $C_{18}$ olefin.

According to the process of this invention, the above olefin mixture is hydrohalogenated with hydrogen bromide in the presence of a free radical catalyst such as an ozonized olefin to produce haloalkanes by anti-Markownikoff addition. Typical haloalkane intermediates of this invention include 1-bromooctane, 1-bromododecane, 1-bromotetradecane, 1-bromooctadecane, 1-bromohexadecane, and the like.

The haloalkanes are then selectively dehydrohalogenated whereby 1-haloalkanes are substantially unaffected while secondary haloalkanes are converted to olefins. The 1-haloalkanes are subjected to amination with amine having at least one replaceable hydrogen atom to form amine hydrohalides. The amine hydrohalides are subsequently converted to the alkylamine product, preferably by a neutralization reaction with a suitable base, e.g. NaOH, KOH, Ca(OH)$_2$, and the like, which forms a halide salt of the base used in the neutralization step, and the alkylamine product thus produced is recovered from the salt.

The amine reactant used to aminate the 1-haloalkane intermediate is ammonia or a lower mono- or dialkyl or cycloalkyl monoamine having from 1 to about 6 carbon atoms per alkyl group. Representative amines include methylamine, ethylamine, n-propyl-amine, isopropylamine, n-butylamine, and isobutylamine, dimethylamine, diethylamine, di-n-propylamine, diisopropylamine, di-n-butylamine, and diisobutylamine. Preferably, the amine reacted with the 1-haloalkane is a short chain secondary amine such as methylamine, dimethylamine, isopropylamine, or diisopropylamine. Most preferably, the amine is methylamine or dimethylamine.

Preferably, the hydrohalogenation step is performed at a temperature of from about 0° C. to about 75° C. most preferably from about 10° C. to about 50° C. As stated above, this step is carried out in the presence of a free radical catalyst to promote anti-Markownikoff addition of hydrohalide to the olefin.

The temperature for the selective dehydrohalogenation step preferably ranges from about 150° C. to about 300° C., most preferably, from about 220° C. to about 250° C. with the pressure ranging from about 0.5 atmosphere to about 10 atmospheres. A metal oxide catalyst such as magnesium oxide may be used to promote the dehydrohalogenation step if desired.

During the amination step, the temperature typically ranges from about 50° C. to about 200° C., preferably from about 100° C. to about 150° C. The pressure normally ranges from about 10 atmospheres to about 100 atmospheres, preferably from about 30 atmospheres to about 60 atmospheres and the reaction is performed with a 1:1 to a 50:1 molar excess of dialkylamine, preferably at a 10:1 to 15:1 molar excess of dialkylamine.

As noted above, subsequent to the amination reaction, the reaction mass is neutralized preferably with an alkaline or alkaline earth metal hydroxide such as NaOH. Such neutralization of the alkylamine hydrohalide to form alkylamine product is not to be confused with the post-treating or heat-treating step which provides a decrease in the amount of flocculent which may form during transportation and/or storage of the alkylamine product. Accordingly, the neutralization step is conducted at a temperature in the range of from about 120° C. to about 160° C. Sufficient alkaline or alkaline earth metal hydroxide is provided during the neutralization step to provide a slight molar excess of hydroxide based on the moles of alkylamine hydrohalide to be converted to alkylamine product. Such molar excess of hydroxide may range from about 3 to about 10% molar excess based on the total number of moles of alkylamine hydrohalide to be neutralized. Typically, a molar excess of 6% hydroxide is sufficient to neutralize essentially all of the alkylamine hydrohalide.

The improvement of the above process embodied in this invention entails contacting the neutralized alkylamine product with aqueous alkaline or alkaline earth metal hydroxide at a temperature and for a period of time sufficient to minimize the formation of floc during the storage and/or transportation of the alkylamine product. While it is preferred to employ this step as a post-treatment step, subsequent to the neutralization step and product purification by distillation, treatment of the alkylamine product with aqueous alkaline or alkaline earth metal hydroxide may also take place before the product is distilled.

The term "minimize" is used to denote that the product thus heat-treated or post-treated contains an amount of floc which does not adversely impact the product turbidity after the product has been stored for about 30 days at room temperature. Such products with minimum floc levels typically have a turbidity value of less than about 10 Nephelometric Turbidity Units (NTU), more preferably, less than 5 NTU, and most preferably from about 0.1 to about 3 NTU. Alkylamine products which have not been heat-treated according to the process of this invention may have turbidity values of greater than 10 NTU after 30 days storage at room temperature.

In the improvement step in the process of this invention, the alkaline or alkaline earth metal hydroxides which may be used include NaOH, KOH, $Mg(OH)_2$, $Ca(OH)_2$ and the like. Preferably, the alkaline or alkaline earth metal hydroxide is aqueous NaOH or KOH. Most preferably, the alkaline or alkaline earth metal hydroxide is NaOH.

The concentration of the aqueous alkaline or alkaline earth metal hydroxide used for the heat-treatment or post-treatment step can range from about 0.1 wt. % to about 100 wt. %. Preferably, the concentration ranges from about 2 wt. % to about 30 wt. %. Most preferably, the alkaline or alkaline earth metal hydroxide is about 25 wt. % NaOH and about 75 wt. % water.

The temperature during the heat-treating step may range from about 170° C. to about 270° C. Preferably, the temperature ranges from about 180° C. to about 240° C. Most preferably, the temperature ranges from about 225° C. to about 235° C.

As the temperature for heat-treating step is increased, shorter heating times may be used since the time for heat-treatment is dependent on the heat-treating temperature thus selected. Accordingly, heat-treatment may be carried out over a time span of about 0.1 hours to about 4 hours. Preferably, the alkylamine product is heat-treated in the presence of the metal hydroxide for about 1 hour to about 2 hours; most preferably about 1.5 hours.

As indicated above, contacting of the alkylamine product with an alkaline or alkaline earth metal hydroxide at a temperature above about 160° C. may take place at various points within the alkylamine manufacturing process, or after the alkylamine product has been purified by distillation. Preferably, the alkylamine product has been neutralized prior to post-treatment or heat-treatment of the product. However, this invention is not limited to such post-treatment of the alkylamine product, as some benefit in reducing the tendency for the product to form floc may be obtained by combining the heat-treatment and neutralization steps. By "post-treatment" is meant treatment of the alkylamine product subsequent to product formation and neutralization.

In the following examples illustrating the product and process of this invention, Fourier transform 1H-NMR data were obtained using a General Electric Model QE-300 spectometer in CDC13, using tetramethylsilane as an internal standard. Chemical shifts are reported using the (δ) scale and coupling constants are reported in Hertz (Hz). Analyses by gas chromatography were done on a Varian Vista Series Model 3700 gas chromatograph, equipped with a flame ionization detector. The column used was an OV-101 column, 30 meters in length obtained from J and W Scientific. Helium was used as the carrier gas (97 ml/min; splitter on) and the column oven was programmed from an initial temperature of 60° C., held 2 minutes, and increased at a rate of 5° C./min. to a final temperature of 200° C.

The term "$C_{12}$ ADMA" is used to signify an alkyldimethylamine product in which the alkyl group contains twelve carbon atoms. Similarly, the term "$C_{14}$ ADMA" is used to denote an alkyldimethylamine product in which the alkyl group contains fourteen carbon atoms and "$C_{16}$ ADMA" contains sixteen carbon atoms in the alkyl group.

EXAMPLE I

Heat treatment of 1-dodecyl dimethylamine ($C_{12}$ ADMA)

During the preparation of 1-Dodecyl dimethylamine ($C_{12}$ ADMA), generally in accordance with the method disclosed in U.S. Pat. No. 4,024,189, a 3.785 liter sample of the product column feed and 0.47 liters of distillate containing 1-dodecyl dimethylamine and a flocculent precipitate were collected. Turbidity values were determined (as described below) for both the distillate sample and product column feed at the time the samples were obtained (Table 1). A portion of the product column feed sample (350 mL) was charged into a 500 mL three-necked round bottom flask and vacuum distilled under the conditions indicated in Table 3. Typically 200–300 mL of the product column feed were obtained as a center cut after 50 mL of distillate was first obtained and the turbidity value of the center cut was determined when the distillation was complete (see Table 1). An additional 350 mL of the $C_{12}$ ADMA product column feed sample was heat-treated with caustic at elevated temperature by charging the product column feed sample into a 600 mL autoclave along with 11 mL of 25% aqueous NaOH. This mixture was allowed to react at 205° C. at a pressure of 0.65 MPa (95 psia) for 1.5 hours. The heat-treated sample was removed and the organic phase was separated using a 500 mL separatory funnel and subsequently water-washed with 50 mL of water and re-separated into an organic portion and an aqueous portion. The organic portion from the NaOH treatment was charged to a 500 mL three-necked round bottomed flask and vacuum distilled under the conditions indicated in Table 3. Typically 200–300 mL of NaOH treated sample were obtained as a center cut after 50 mL distillate was first obtained and turbidity value was determined on the treated sample when the distillation was complete (Table 1). All samples were retained 30 days (to simulate overseas shipments) at room temperature (20°–26° C.), after which time turbidity values were again determined (Table 2).

EXAMPLES II

Heat treatment of 1-tetradecyl dimethylamine ($C_{14}$ ADMA)

The procedure of Example 1 was generally followed except that the product to be post-treated was 1-tetradecyl dimethylamine ($C_{14}$ ADMA) and the distilled product column feed sample was reacted with 25 wt. % NaOH at 215° C. and a pressure of 0.79 MPa (115 psia) for 1.5 hours. As in Example 1, the samples were retained 30 days (to simulate overseas shipments) at room temperature (20°–26° C.), after which time turbidity values were measured (Table 2).

EXAMPLE III

Heat treatment of 1-hexadecyl dimethylamine ($C_{16}$ ADMA)

The procedure of Example 1 was generally followed except that the product to be post-treated was 1-hexadecyl dimethylamine ($C_{16}$ ADMA) and the distilled product column feed sample was reacted with 25 wt. % NaOH at 204° to 216° C. and a pressure of 0.79 MPa (115 psia) for 1.5 hours. As in Example 1, the samples were retained 30 days (to simulate overseas shipments) at room temperature (20°–26° C.), after which time turbidity values were measured (Table 2).

EXAMPLES IV

Heat treatment of 1-tetradecyl dimethylamine ($C_{14}$ ADMA)

The procedure of Example 1 was generally followed except that the product to be post-treated was 1-tetradecyl dimethylamine ($C_{14}$ ADMA) and the distilled product column feed sample was reacted with 40 mL of 25 wt. % NaOH at 220° to 230° C. and a pressure of 1.34 to 1.55 MPa (195 to 225 psia) for 1.5 hours. As in Example 1, the samples were retained 30 days (to simulate overseas shipments) at room temperature (20°–26° C.), after which time turbidity values were measured (Table 2).

TABLE I

Turbidity of ADMA Samples at Time of Distillation

| Example No. | PCF[1] (NTU) | Distillate (NTU) | Distilled PCF[1] (NTU) | PCF[1] Heat-Treated and Distilled (NTU) |
|---|---|---|---|---|
| I | 37 | 10.5 | 6 | 1 |
| II | 2.5–3.0 | 23 | 7.5–8.5 | 1.8 |
| III | 8.9 | 9 | 3.5 | 1.2 |
| IV | 4.1 | 9–10 | 21–22 | 1.1[2] |

[1]Product Column Feed
[2]Distilled at 210° C. and 53 mm Hg vacuum

TABLE II

Turbidity of ADMA Samples after 30 Days Storage (at 20° to 26° C.)

| Example No. | PCF[1] (NTU) | Distillate (NTU) | Distilled PCF[1] (NTU) | PCF[1] Heat-Treated and Distilled (NTU) |
|---|---|---|---|---|
| I | 45 | 10 | 8.7 | 1.5 |
| II | 4.8 | 27 | 3.8 | 1.3 |
| III | 24.0 | 12.0 | 3.2 | 1.7 |
| IV | 1.2 | 17.0 | 18 | 0.8[2] |

[1]Product Column Feed
[2]Distilled at 210° C. and 53 mm Hg vacuum

In the above Tables I and II, it is particularly noted that the heat-treated samples not only had low turbidity values even after storage for 30 days, but the samples remained clear and very little precipitate formed. The turbidity values are indicative of the presence of floc in the samples. In contrast, precipitate formed immediately in both lab and plant samples which had not been heat-treated with NaOH. Thus, the product quality of ADMA can be significantly improved by the process of this invention.

TABLE III

Distillation Conditions for the ADMA Samples

| Example No. | Plant Distillate Temp. (°C.) | Lab Distilled PCF[1] Overhead[3] Temp. (°C.) | Lab Distilled PCF[1] Bottoms[3] Temp. (°C.) | Lab Distilled PCF[1] Vacuum[3] (mm Hg) |
|---|---|---|---|---|
| I | 195 | 170 | 190–212 | 67 |
| II | 207 | 215 | 240 | 142 |
| III | 235 | 230 | 235–240 | 65 |
| IV | 209 | 220 | 240 | 148 |

[1]Product Column Feed
[2]Post-treated and distilled product column feed.

Method for Determining Turbidity

In a generalized procedure for turbidity measurements, bulk quantities of each liquid sample (200–300 mL) were mixed by rapid inversion five times in succession. Then a portion of the mixed sample (35 mL) was charged to a cylindrical cell (9.5 mm×2.2 mm) and allowed to settle approximately 3 minutes at room temperature (typically 20°–26° C.). The turbidity values were then measured relative to precalibrated 5 and 10 NTU standards using a Turbidimeter Model 51-8053 Turbidity Meter.

In accordance with the foregoing examples, it is believed that the effects of time, temperature and/or caustic concentration are critical to obtaining the improvements of the present invention.

Variations of the invention are within the spirit and scope of the appended claims.

What is claimed is:

1. In a process for producing alkylamine from olefin by hydrohalogenating said olefin to form haloalkane and reacting said haloalkane with amine to form said alkylamine, the improvement comprising heat-treating said alkylamine in the presence of an aqueous alkaline or alkaline earth metal hydroxide at a temperature and for a period of time sufficient to minimize the formation of flocculent precipitate during storage of said alkylamine.

2. The process of claim 1 wherein said alkylamine is alkyldimethylamine or dialkylmethylamine.

3. The process of claim 1 wherein said olefin is selected from $C_8$–$C_{18}$ olefins.

4. The process of claim 3 wherein said amine is selected from the group consisting of $C_1$–$C_6$ alkylamines, $C_3$–$C_6$ cycloalkylamines, $C_1$–$C_6$ dialkylamines, $C_3$–$C_6$ dicycloalkylamines and mixtures thereof.

5. The process of claim 4 wherein said amine is dimethylamine or methylamine.

6. The process of claim 5 wherein said aqueous alkaline or alkaline earth metal hydroxide is aqueous 25% NaOH.

7. The process of claim 1 wherein said aqueous alkaline or alkaline earth metal hydroxide is aqueous 25% NaOH.

8. A method for reducing the potential for forming flocculent precipitate during the manufacture and/or storage of alkylamines, said method comprising heat-treating said alkylamine in the presence of an alkaline or alkaline earth metal hydroxide at a temperature and for a period of time sufficient to minimize the formation of said flocculent precipitate during manufacture and/or storage of said alkylamine.

9. The method of claim 8 wherein said alkyl amine is alkyldimethylamine or dialkylmethylamine wherein the alkyl group contains from 8 to 18 carbon atoms.

10. The method of claim 9 wherein said alkaline or alkaline earth metal hydroxide is NaOH.

11. The method of claim 8 wherein said temperature is within the range of from about 180° to about 240° C.

12. The method of claim 10 wherein said temperature is within the range of from about 180° to about 240° C.

13. A process for preparing alkylamine comprising:
(a) hydrobrominating mixed olefin containing α and internal olefins in the presence of a free radical catalyst so as to form a mixture of primary and secondary bromoalkanes;
(b) selectively dehydrobrominating said secondary bromoalkanes and separating said dehydrobrominated secondary bromoalkanes from said primary bromoalkanes;
(c) Aminating said primary bromoalkanes with amine to form alkylamine hydrobromides;
(d) neutralizing said alkylamine bromohalides with NaOH to form alkylamine product; and
(e) heat-treating said alkylamine product with an alkaline or alkaline earth metal hydroxide at a temperature and for a period of time sufficient to minimize the formation of flocculent precipitate during storage of said alkylamine product.

14. The process of claim 13 wherein said alkylamine product is alkyldimethylamine or dialkylmethylamine.

15. The process of claim 13 wherein said mixed olefin is selected from $C_8$–$C_{18}$ olefins.

16. The process of claim 15 wherein said amine is selected from the group consisting of $C_1$–$C_6$ alkylamines, $C_3$–$C_6$ cycloalkylamines, $C_1$–$C_6$ dialkylamines, $C_3$–$C_6$ dicycloalkyl-amines, and mixtures thereof.

17. The process of claim 16 wherein said alkaline or alkaline earth metal hydroxide is NaOH.

18. The process of claim 17 wherein the temperature for step (e) is in the range of from about 180° to about 240° C.

* * * * *